Figure 3:
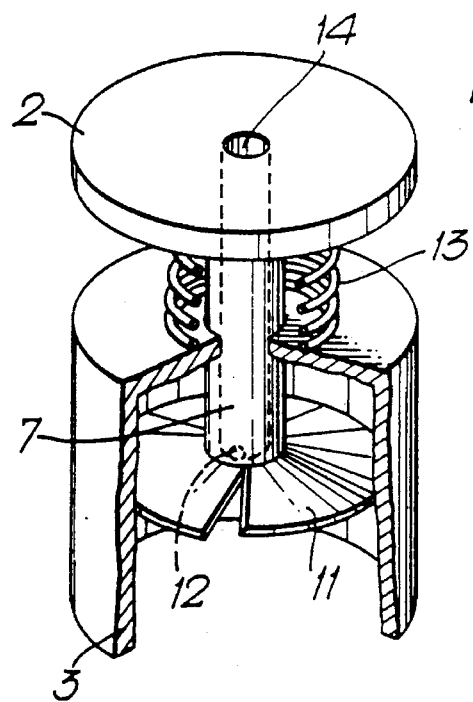

United States Patent [19]

Clark et al.

[11] Patent Number: 5,482,946
[45] Date of Patent: Jan. 9, 1996

[54] MEDICAMENT INHALATION DEVICE AND FORMULATION

[75] Inventors: Andrew R. Clark, Loughborough; John L. Hart, Bramcote, both of Great Britain

[73] Assignee: Fisons plc, Ipswich, England

[21] Appl. No.: 294,138

[22] Filed: Aug. 22, 1994

Related U.S. Application Data

[62] Division of Ser. No. 897,246, Jun. 11, 1992, Pat. No. 5,341,800, which is a division of Ser. No. 759,711, Sep. 12, 1991, Pat. No. 5,176,132, which is a continuation of Ser. No. 531,254, May 31, 1990, abandoned.

[30] Foreign Application Priority Data

May 31, 1989 [GB] United Kingdom .................. 8912503
Jun. 10, 1989 [GB] United Kingdom .................. 8913392

[51] Int. Cl.⁶ ................ A61K 9/14; A61K 31/135; A61K 31/195; A61K 31/35
[52] U.S. Cl. ............ 514/291; 128/203.15; 128/203.21; 424/46; 424/464; 424/489; 514/457; 514/653; 514/826
[58] Field of Search ............ 424/464, 46, 489; 514/457, 653, 826, 291

[56] References Cited

U.S. PATENT DOCUMENTS

| 3,957,965 | 5/1965 | Hartley et al. | 424/14 |
| 4,515,805 | 5/1985 | Newman et al. | 514/460 |
| 4,940,588 | 7/1990 | Sparks et al. | 424/490 |

OTHER PUBLICATIONS

Grimwood et al. *Chem. Abst.* 94:162640 (1981).

*Primary Examiner*—Peter O'Sullivan
*Attorney, Agent, or Firm*—Marshall, O'Toole, Gerstein, Murray & Borun

[57] ABSTRACT

A compacted body of powdered medicament for use in a device for the administration by inhalation of a medicament in powdered form. The compacted body is made by compressing a loose powder containing the medicament in powdered form under pressure to create sufficient structural integrity in the body to permit metering of several unit doses of the medicament by abrasion of the body in the device.

5 Claims, 3 Drawing Sheets

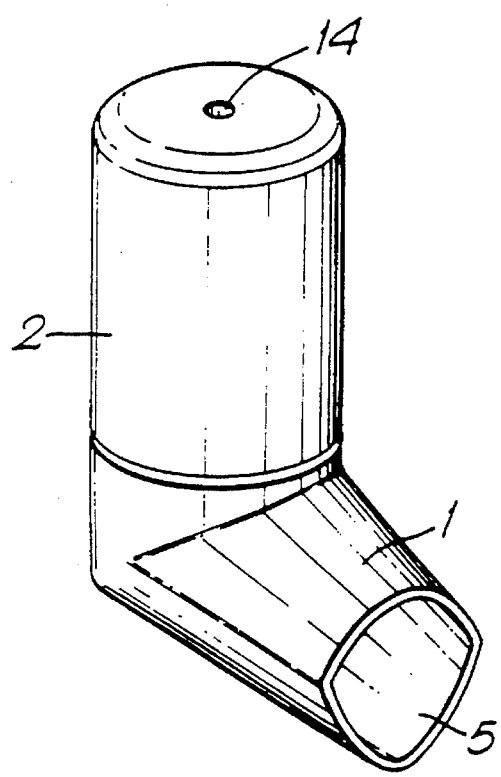
Fig. 1.
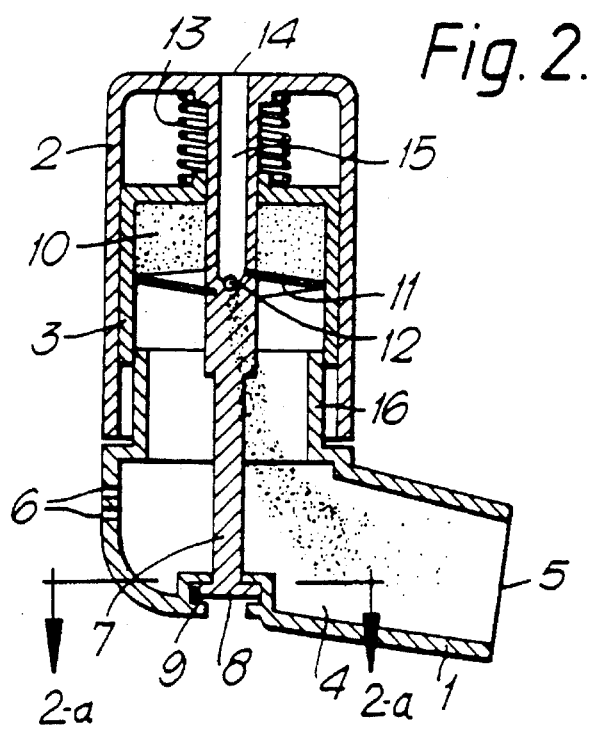
Fig. 2.
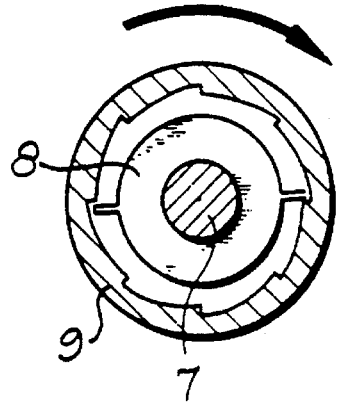
Fig. 2-a
DOSE DIRECTION

MEDICAMENT INHALATION DEVICE AND FORMULATION

This is a divisional of U.S. application Ser. No. 07/897,246, filed Jun. 11, 1992, now U.S. Pat. No. 5,341,800, issued Aug. 30, 1994; in turn a divisional of Ser. No. 07/759,711 filed Sep. 12, 1991 (now U.S. Pat. No. 5,176,132 issued Jan. 5, 1993); in turn a Cont. of Ser. No. 07/531,254 filed May 31, 1990 (now abandoned).

This invention relates to a device for the administration of powdered medicaments by inhalation, more particularly to a multiple-dose device with metering means for the dispensing of doses from a medicament reservoir, and also to medicament formulations for use therein.

BACKGROUND OF THE INVENTION

The administration by inhalation of medicaments in dry powder form is well known. Devices for the metering and dispensing of measured doses of medicament from a reservoir have also been described previously (for example in UK Patent No 2041763). Such devices typically comprise a medicament reservoir and a metering chamber with a volume chosen such that, when filled, the chamber contains the desired weight of medicament for one dose. Filling of the metering chamber is generally accomplished under the influence of gravity, the chamber typically being located at the bottom of the reservoir. Such devices have the disadvantage that variations in the density of the metered powder can easily occur resulting in inaccurate or inconsistent dosing. The packing density of the powder may also depend on the weight of powder remaining in the reservoir, leading to a gradual reduction in the dose delivered by the device. In addition, the dose metered is strongly dependent on the orientation of the device.

Furthermore, when the medicament to be administered is hygroscopic, great care must be taken to ensure that water does not contaminate the medicament because this may cause lumps of medicament to form which can clog the device and lead to inconsistent dosing. The problem of water uptake by hygroscopic medicaments is overcome to some extent by supplying them in gelatin capsules which are punctured immediately prior to administration in a suitable device (for example the device of UK Patent 1122284). However, a fresh capsule must be inserted into the device for each dose, and the volume occupied by a month's supply of capsules is considerable. In addition, such devices have the further disadvantage that their performance is dependent upon the relative humidity of the atmosphere in which they are used, ie the quality of the cloud (the proportion of particles in the cloud which are fine enough to penetrate deep into the lung) decreases as the relative humidity increases. Furthermore, if the gelatin capsules are stored in an atmosphere of high relative humidity, they become soft and consequently difficult to handle.

SUMMARY OF THE INVENTION

We have now found that these disadvantages can be overcome or substantially mitigated by the use of a metering means which relies not on gravitational force to fill a metering chamber, but on abrasion of a compacted body of powdered medicament.

Thus, according to a first aspect of the present invention, there is provided a device for the administration by inhalation of a medicament in powdered form, comprising a medicament reservoir and metering means for dispensing a dose of medicament from the reservoir, characterized in that the reservoir comprises a compacted body of powdered medicament and the metering means includes means for abrading the compacted body.

By "compacted body of powdered medicament" we mean a body of medicament produced by compressing a sample of loose powder so that the medicament particles hold together. The degree of compaction obtained will clearly depend upon the compression force applied to the sample of loose powder, and the term "compacted body of powdered medicament" includes compacted bodies of medicament ranging from those that are loosely compacted to those that are tightly compacted.

A loosely compacted body of medicament may be obtained by applying a pressure of, for example, from $1 \times 10^4$ to $15 \times 10^4$ $Nm^{-2}$ to a sample of loose powder (for example a compression force as might be applied by biasing means in certain embodiments of the first aspect of the present invention), and the degree of compaction would be insufficient for such bodies to retain their structural integrity upon handling.

A tightly compacted body of medicament may be obtained by applying a pressure of, for example, from $30 \times 10^4$ to $150 \times 10^4$ $Nm^{-2}$ to a sample of loose powder (for example a compression force as might be applied by a small hydraulic press), and the degree of compaction would be sufficient for such bodies to retain their structural integrity upon handling.

The medicament may consist solely of an active ingredient, for example a hygroscopic drug. Active ingredients which may be mentioned include sodium cromoglycate, nedocromil sodium, salbutamol and terbutaline. We prefer the medicament to additionally comprise an inert carrier, especially in the case of tightly compacted bodies of medicament, because this results in improved compaction and dispersion characteristics. Suitable inert carriers include sugars, for example lactose. When an inert carrier is present we prefer the particle size of the carrier to be larger than that of the active ingredient. Suitable particle sizes for the active ingredient when in loose powder form are from 1 to 10 μm.

Formulations of the medicament which may be mentioned include a mixture of any one of the above-mentioned active ingredients in association with lactose, the proportions of carrier to active ingredient depending upon the particular substances present. For example, we have found that a 1:1 mixture of nedocromil sodium or sodium cromoglycate with lactose is advantageous.

Tightly compacted bodies of powdered inhalation medicament are novel and form a second aspect of the present invention. This second aspect of the invention also includes compacted bodies comprising more than one active ingredient, and compacted bodies comprising more than one inert carrier.

The compacted body of inhalation medicament may have any convenient external shape, for example cylindrical or brick-like, and in the case of a loosely compacted body will generally be determined by the inner configuration of the medicament reservoir.

Desirably, the means for abrading includes a blade which cuts, scrapes or otherwise erodes a surface of the compacted body by relative rotation or sliding between them. For example, the blade may have a helical shape, in which case the dose abraded from the compacted body of medicament will depend upon the pitch of the helix, the diameter of the blade, the density of the compacted body, and the angle through which the blade is rotated. Thus, when the device is provided with a helical blade, we prefer it to be further provided with blade rotation control means, for example a ratchet which will only permit rotation through a predetermined angle for each dose.

The compacted body may be moved towards the abrading means by a predetermined distance to permit the correct amount of medicament to be removed for one dose. This movement may be achieved by screw means (for example a mechanism similar to that used in lipsticks or glue in stick form) or by biassing means such as a spring urging the compacted body towards the abrading means. Alternatively, the compacted body may be fixed and the abrading means may move towards it.

The inner surfaces of devices according to the first aspect of the invention which are in contact with the compacted body of medicament (for example the abrading means and the interior of the reservoir) may advantageously be coated with a friction reducing agent, for example PTFE (Polytetrafluoroethylene).

We prefer devices according to the first aspect of the invention to include a through-going pathway connecting an air inlet with an air outlet, for example a mouthpiece such that, in use, a metered dose of medicament is deposited in the through-going pathway and is then inhaled by a patient inhaling at the air outlet.

We have also found a particular arrangement of air passageways (referred to herein as 'cyclone means') which is especially useful in inhalation devices according to the first aspect of the present invention and also in other devices for the administration of powdered inhalation medicaments. Such cyclone means have been found to help improve the quality of the medicament cloud delivered to a patient. Thus, according to a third aspect of the present invention there is provided a device for the administration by inhalation of a medicament in powdered form, comprising a through-going pathway including a chamber within which entrained medicament may circulate, wherein the inlet from the pathway to the chamber is tangential to the chamber wall and orthogonal to the longitudinal axis of the chamber, and the outlet from the chamber is situated on the longitudinal axis of the chamber so that entrained medicament is preferentially removed through the outlet from the central zone of the chamber, characterized in that the inlet passageway includes a venturi adjacent to the junction of the inlet passageway with the chamber.

When cyclone means are used in association with devices according to the first aspect of the present invention, the metered dose is preferably deposited in the through-going pathway upstream from the inlet to the chamber. A patient then inhales through a mouthpiece communicating with the outlet from the chamber and thus inhales the medicament which is entrained in the resulting airstream. Such cyclone means have the advantage that the finer particles in a particle population are selected for inhalation. They also cause the bolus of entrained powder to be spread out more evenly so that the dose of medicament is inhaled over a longer period of time.

Other means for improving the quality of the medicament cloud which may be provided in the through-going pathway include grids, propellers and vanes through which air and entrained medicament pass.

The devices of the present invention overcome the disadvantages of prior art devices in that a month's supply of medicament occupies a much smaller volume than, for example, an equivalent number of gelatin capsules. In addition, we have surprisingly found that the quality of the medicament cloud produced by devices of the present invention charged with compacted bodies of medicament according to the second aspect of the invention is not affected by the relative humidity of the atmosphere in which they are used, the performance remaining comparable with, and in some cases superior to the device of UK Patent 1122284 when it is operated in an atmosphere of low relative humidity. We have also unexpectedly found that such devices may be stored in an atmosphere of high relative humidity without adversely affecting the quality of the medicament cloud eventually obtained from them.

Further, the devices of the present invention have the advantage that they are very simple to use, in some embodiments a twist of the medicament-compact holding chamber being all that is required before inhaling through the mouthpiece. Also, the dosing consistency is much greater than is found with devices in which filling of a metering chamber is accomplished under the influence of gravity (as in the device of UK Patent No 2041763). In addition they do not have the disadvantage that actuation of the device must be synchronised with inhalation as with pressurized aerosol devices.

Although the invention has been described for use in oral inhalation of medicaments, it is also suitable for the administration of nasal medicaments by inhalation. The necessary adaptation for this mode of administration will be readily apparent to those skilled in the art.

The devices of the present invention may be designed for limited use (ie supplied with an integral compacted body of medicament and discarded when that is exhausted), or to be reusable (ie replacement compacted bodies may be inserted).

BRIEF DESCRIPTION OF THE DRAWINGS

Preferred embodiments of the present invention will now be described, by way of example, with reference to the following drawings, in which corresponding features are given the same reference numeral:

FIG. 1 is a perspective view of an inhalation device according to the first aspect of the invention;

FIG. 2 is vertical cross sectional view of the device of FIG. 1;

FIG. *2a* is a partial sectional view on an expanded scale along the line *2a*—*2a* of FIG. 2 showing a ratchet mechanism which limits the rotation of the helical blade shown in FIG. 2.

FIG. 3 is a perspective view of the medicament reservoir and metering means of the device of FIG. 1, partly cut away;

FIG. 4 is an alternative embodiment of a device according to the first aspect of the invention;

FIG. 5 is a schematic view of an arrangement of air passageways in a device according to the third aspect of the invention;

FIG. 6 is a lateral cross sectional view of the arrangement of FIG. 5 in the plane VI—VI—VI; and FIG. 7 is a vertical cross sectional view of a device incorporating the first and third aspects of the invention.

DESCRIPTION OF THE PREFERRED EMBODIMENTS

Referring first to FIGS. 1 and 2, a device according to the first aspect of the invention comprises a lower body portion 1, and an upper body portion 2 which encloses a medicament reservoir 3.

Lower body portion 1 defines a tubular chamber 4 having an opening 5 in a mouthpiece portion. Air inlets 6 are provided in the wall of lower body portion 1 opposite opening 5.

Upper body portion 2 is generally cylindrical and is rotatably mounted on lower body portion 1 over a second opening therein by an axial shaft portion 7 having a flanged end 8 which is received by a socket 9 provided in the lower wall of lower body portion 1.

Medicament reservoir 3 is also generally cylindrical, and is slidably mounted in upper body portion 2. Shaft 7 passes axially through reservoir 3 and also through an axial bore formed in a cylindrical block of tightly compacted medicament 10 which is situated in reservoir 3.

A helical blade 11 is attached to shaft 7 towards the middle of its length and extends radially to the inner wall of reservoir 3. The edge of blade 11 describes an arc of approximately 350°, and a further air inlet 12 is positioned between the leading and trailing edges of blade 11. Air inlet 12 communicates with an external opening 14 situated in the center of the upper face of upper body portion 2 via passageway 15 which runs axially through shaft 7.

The block of compacted medicament 10 is urged towards blade 11 by spring 13 which acts against the inner wall of upper body portion 2 and the outer wall of reservoir 3.

To use the device, upper body portion 2 is rotated through 45°, further rotation being prevented by a ratchet mechanism shown in FIG. 2a, resulting in blade 11 cutting into block of medicament 10 and abrading the quantity of medicament required for one dose. Some of the abraded medicament is deposited in lower body portion 1, and some remains between the leading and trailing edges of blade 11. A patient then inhales through opening 5, causing air to be drawn in through inlets 6 and opening 14, resulting respectively in medicament being entrained from lower body portion 1 and from between the leading and trailing edges of blade 11. The entrained medicament is then inhaled by the patient.

It will be appreciated that upper body portion 1 is stabilized by the wall of medicament reservoir 3 sliding telescopically over a peripheral wall 16 formed around the second opening in lower body portion 1 as the block of medicament 10 is abraded. If necessary, cooperating vertical tongues and grooves may be provided on the inner and outer faces of the wall of medicament reservoir 3 and peripheral wall 16 in order to prevent relative rotation between them, which would reduce the effectiveness of blade 11.

Figure 4:
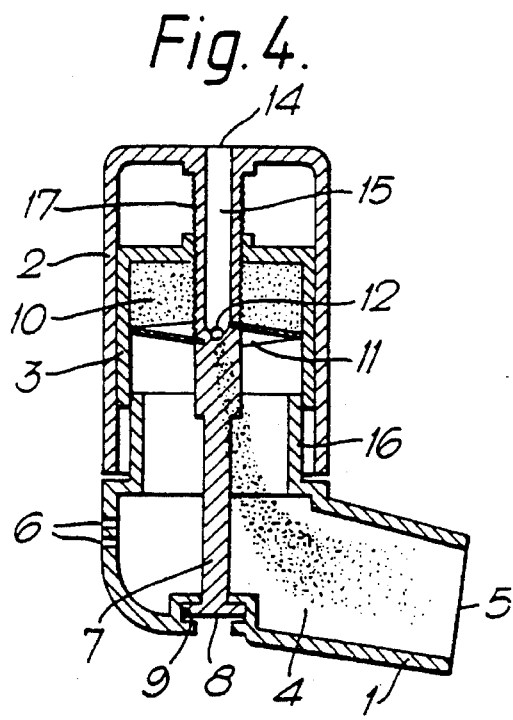

Referring now to FIG. 4, an alternative embodiment resembles that of FIG. 1, except that medicament reservoir 3 is moved towards blade 11 by the action of a screw thread 17 formed on the upper portion of shaft 7 upon which the upper opening of medicament reservoir 3 is threaded. The length of block 10 abraded by blade 11 as it turns through a certain angle coincides with the distance which medicament reservoir 3 is moved down shaft 7 by the action of screw thread 17.

Figure 5:
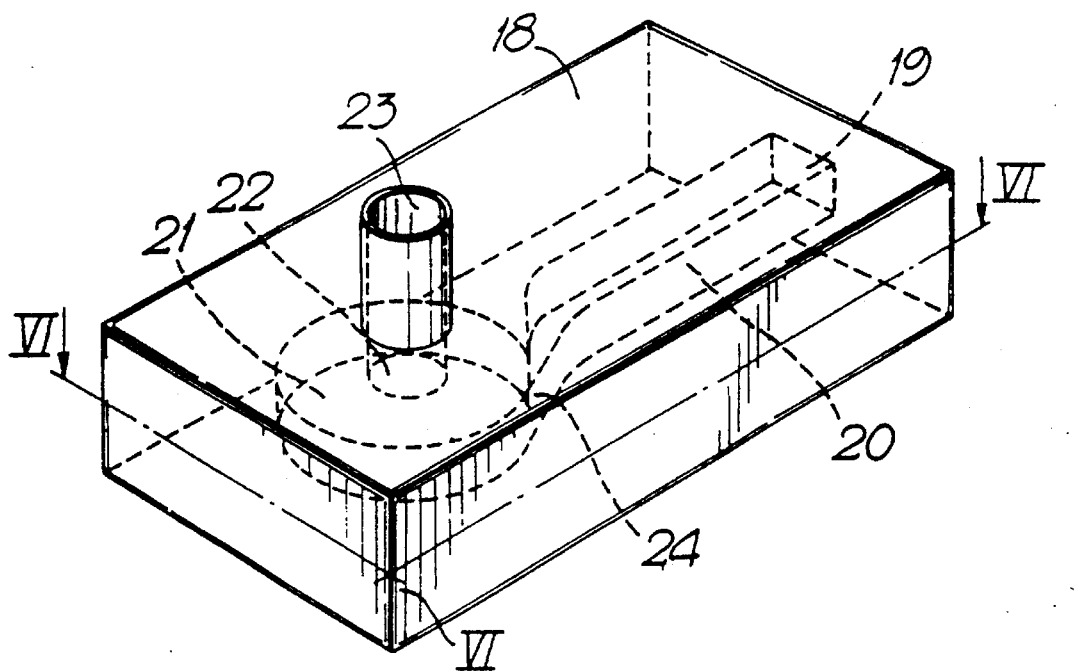
Figure 6:
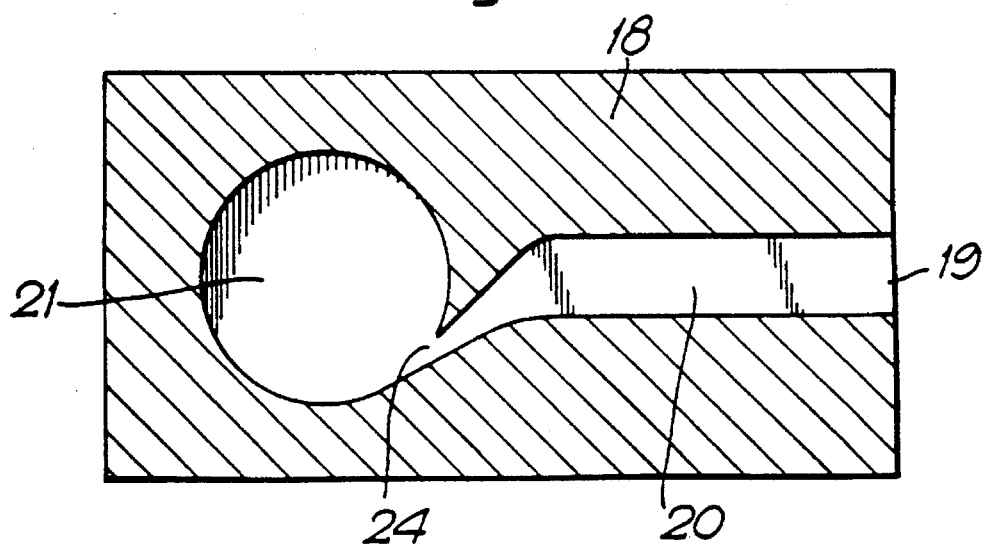

Referring now to FIGS. 5 and 6, a device according to the third aspect of the invention comprises a body 18 provided with an air inlet 19 which communicates via an inlet passageway 20 with a cylindrical chamber 21 into which the inlet passageway 20 empties tangentially; an outlet passageway 22 situated on the longitudinal axis of the chamber, the diameter of the outlet passageway's opening being about one third that of the chamber; and a mouthpiece 23 situated at the end of the outlet passageway. Inlet passageway 20 is orthogonal to outlet passageway 22. Adjacent to the junction of inlet passageway 20 with chamber 21, there is a local constriction (venturi) 24 in the inlet passageway.

To use the device illustrated in the drawings, a dose of medicament is deposited in inlet passageway 20 (by means not shown) adjacent to air inlet 19. A patient then inhales through mouthpiece 23 which causes air to be drawn into inlet passageway 20. The inhaled stream of air entrains the medicament, which then passes into cylindrical chamber 21 from which it leaves through outlet passageway 22 and is then delivered to the patient's mouth through mouthpiece 23.

Figure 7:
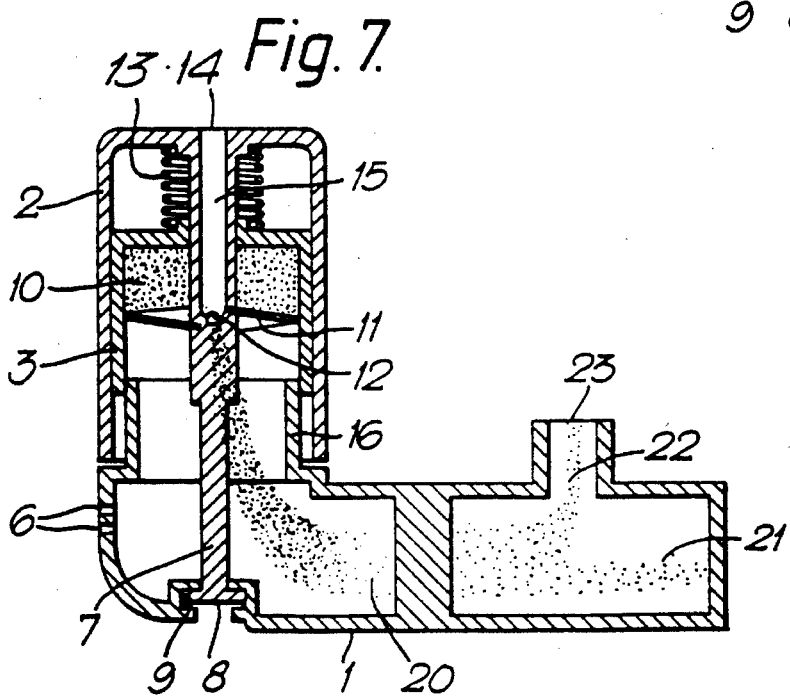

Referring now to FIG. 7, an inhalation device comprises the features of the device shown in FIG. 1 with the arrangement of air passageways shown in FIG. 5 being incorporated into lower body portion 1. In use, a dose of medicament is abraded from block of medicament 10 and deposited in inlet passageway 20. A patient then inhales at mouthpiece 23.

We claim:

1. A tightly compacted body of powdered inhalation medicament for administration from an inhalation device, comprising:

a loose powder including an active ingredient having a particle size of from 1 to 10 µm compressed to form said tightly compacted body;

the degree of compression being sufficient to impart said tightly compacted body with structural integrity such that a plurality of unit doses of medicament can be metered therefrom by abrasion.

2. A tightly compacted body according to claim 1 compressed by applying a pressure of from $30 \times 10^4$ to $150 \times 10^4$ $Nm^{-2}$ to the loose powder.

3. A tightly compacted body according to claim 1 wherein the loose powder contains an inert carrier in addition to the active ingredient.

4. A tightly compacted body according to claim 3 wherein the inert carrier is lactose.

5. A tightly compacted body according to claim 1 wherein the active ingredient is selected from the group consisting of sodium cromoglycate and nedocromil sodium.

* * * * *